US007040960B2

(12) United States Patent
Hench et al.

(10) Patent No.: US 7,040,960 B2
(45) Date of Patent: May 9, 2006

(54) USE OF BIOACTIVE GLASS FOR CUTTING BIOACTIVE GLASSES

(75) Inventors: Larry L. Hench, London (GB); Ian D. Thompson, London (GB); Richard J. Cook, London (GB); Timothy F. Watson, London (GB); Paul D. Robinson, London (GB)

(73) Assignees: King's College London, London (GB); Imperial College Innovations Limited, London (GB)

( * ) Notice: Subject to any disclaimer, the term of this patent is extended or adjusted under 35 U.S.C. 154(b) by 0 days.

(21) Appl. No.: 10/473,410

(22) PCT Filed: Mar. 28, 2002

(86) PCT No.: PCT/GB02/01513

§ 371 (c)(1),
(2), (4) Date: Mar. 11, 2004

(87) PCT Pub. No.: WO02/079108

PCT Pub. Date: Oct. 10, 2002

(65) Prior Publication Data

US 2004/0137827 A1    Jul. 15, 2004

Related U.S. Application Data

(60) Provisional application No. 60/281,809, filed on Apr. 6, 2001.

(30) Foreign Application Priority Data

Mar. 30, 2001  (GB)  .................................. 0108115.7

(51) Int. Cl.
*B24B 1/00*    (2006.01)
(52) U.S. Cl. .......................................... 451/38; 451/41
(58) Field of Classification Search .................. 451/38, 451/39, 40, 41, 42, 44
See application file for complete search history.

(56) References Cited

U.S. PATENT DOCUMENTS

| 4,579,530 | A |   | 4/1986  | McLaughlin          |
|-----------|---|---|---------|---------------------|
| 5,249,395 | A | * | 10/1993 | Yoshida ....... 451/35 |
| 5,251,468 | A | * | 10/1993 | Lin et al. ....... 72/53 |
| 5,573,446 | A |   | 11/1996 | Dey et al.          |
| 5,634,956 | A |   | 6/1997  | Suh et al.          |
| 5,934,287 | A |   | 8/1999  | Hayashi et al.      |
| 6,054,400 | A | * | 4/2000  | Brink et al. ....... 501/63 |
| 2002/0098776 | A1 | * | 7/2002 | Dopper ....... 451/2 |
| 2003/0008263 | A1 | * | 1/2003 | Cook et al. ....... 433/215 |

FOREIGN PATENT DOCUMENTS

FR    2543433 A1    10/1984
WO    WO 99/13852 A1    3/1999

* cited by examiner

*Primary Examiner*—Dung Van Nguyen
(74) *Attorney, Agent, or Firm*—Foley & Lardner LLP

(57) ABSTRACT

The present invention relates to a method of cutting a bioactive glass object which comprises contacting the bioactive glass object with bioactive glass particles delivered using an air abrasion system.

18 Claims, 15 Drawing Sheets

USE OF BIOACTIVE GLASS FOR CUTTING BIOACTIVE GLASSES

This application is a 371 of PCT/GB02/01513 filed on Mar. 28, 2002 which claims benefit of 60/281,809 filed on Apr. 6, 2001 abandoned.

The present invention relates to the use of bioactive glasses for cutting and shaping bioactive glasses, particularly bioactive glass implants and tissue engineering scaffolds.

Bioactive glass implants are beginning to gain a wide acceptance in surgery—e.g. "Douek Med" ossicle replacement grafts, for treating (middle ear disease induced) conductive deafness (Hench L. L., 1998, Bioceramics The Centennial Feature, J. Am. Ceram. Soc., 81, 1705–1728), bioactive glass trans cutaneous and trans osseous abutments for cochlear implants for middle ear deafness (Hench L. L., 1998, Bioceramics The Centennial Feature, J. Am. Ceram. Soc., 81, 1705–1728), ERMI—Endosseous Ridge Maintenance Implants to conserve jaw bone height after extraction of remaining teeth (Hench L. L., 1998, Bioceramics The Centennial Feature, J. Am. Ceram. Soc., 81, 1705–1728) and orbital floor (eye socket) repairs after trauma or disease processes (Aitasalo K, Suonpaa J, Kinnunen I, Yli-Urpo A., 1999, Reconstruction of Orbital floor fractures with bioactive glass (S53P4): In Bioceramics 12. Ed Ogushi H, Hastings G W, Yoshikawa T. World Scientific, London, UK. pp 49–52).

However, all such implants suffer from the same principle deficiency—they are difficult to shape after production to better fit the patient's individual needs.

Melt derived bioactive glasses are cast into shape using, for example, graphite moulding techniques. Thus bespoke implants can be cast, although undercuts etc in the final form can only be accommodated by inclusion and careful planning of the mould release mechanism.

Sol-gel glass manufacture involves casting a gel in a rigid mould, which after controlled desiccation becomes a porous monolithic solid product, approximately 50% of the start volume (Hench L. L., West J. K., 1996, Life Chemistry Reports, 13, 187–241). The gel shrinks in the mould during drying and must be freely allowed to contract, otherwise it will tear itself apart during the drying process. Consequently, only the simplest of product shapes can be produced from the sol-gel process.

There is a great surgical morbidity advantage to be gained by shaping an implant to fit the patient, rather than being forced to adapt a patient's anatomy to match an implant allograft. Therefore, if bioactive glass materials are to be employed in the surgical sphere for implantation to aid healing or augment the host's skeletal structure, a mechanism for shaping sol-gel glasses and trimming, refining or adjusting the precast melt derived glasses will be highly desirable.

In adjusting the shape of a bioactive glass object, three basic types of cutting action exist: rotary cutting (e.g. rotating edges chip away at the substrate as in milling), linear sawing (e.g. a plane action, or drawn wire saw action) and individual chipping actions (e.g. intermittent chiselling). However, the application of most rotary and linear cutting techniques to brittle substrates such as bioactive glass objects inevitably cause fracture, long before the finished product emerges.

Similarly, drilling or boring holes in a bioactive glass object—necessary for suturing an implant into position—using a conventional cutting technique, such as rotary drilling or sawing, is, at best, extremely problematic.

Rotary and linear cutting techniques generate large amounts of heat due to the inevitable friction between the cutting surface and the substrate. If excessive heat is generated during a cutting process, material can be transferred from the cutting instrument to the finished product surface thereby tainting it. There is therefore a high risk of poisoning the delicate bioactive glass reaction systems if rotary cutting is employed. Coolant water sprays decrease cutting temperature rises dramatically, however bioactive glass materials cannot be cut using such water sprays and coolants, unless at the immediate point of use, as the bioactivity reaction will be started prematurely and the clinical advantage lost.

Air abrasion offers benefits in cutting vulnerable structures such as bioactive glass objects. However, the presence of alumina (or aluminium), the principle abrasive cutting agent in common use today, above a trace level (>1.5 wt %), will totally inhibit or poison the bioactive reaction upon which the bioactive glass implants rely for their healing success (Hench L. L., Andersson O., 1993, Bioactive glasses. In: An Introduction to Bioceramics Chapter 3 pp41–62. Ed: Hench L L, Wilson J World ScientificPub. Singapore and Oonishi H., Hench L. L., Wilson J., Sugihara F., Tsuji E., Kushitani S., Iwaki H., 1999, J. Biomed. Mater. Res., 44, 31–43).

We have now found that by using bioactive glass particles as an alternative abrasive agent in a conventional air abrasion system, the benefits of air abrasion cutting are retained but the problems of toxicity associated with the use of alumina grit are avoided.

Accordingly the present invention provides a method of cutting a bioactive glass object which comprises contacting the bioactive glass object with bioactive glass particles delivered using an air abrasion system.

The present invention is based upon the observation that when applied through a conventional air abrasion system the bioactive glass particles are able to cut bioactive glass objects to the required shape.

Further advantages arise due to the fact that the bioactive glass particles and fragments thereof which may become embedded in the cut surface of the bioactive glass monolith further encouraging rapid re-mineralisation of the affected area and allowing accelerated healing.

The above invention, will allow production of a low internal stress implant, fitting the patient accurately, and with a surface that is highly suitable for accelerating bony healing, augmenting existing bony surfaces and reconstructive surgical procedures (e.g. middle ear ossicle implants).

To be able to produce more complex shaped products, beyond that possible by casting alone will prove a significant benefit to the employment of bioactive glasses in surgical procedures.

DESCRIPTION OF THE FIGURES

FIG. 2-1. A: illustrates a real-time confocal image of 45S5 Bioglass® being sawn. The reflection of the diamond wire saw (SW) is seen, having produced an extremely ragged and roughened finish surface (F), from which, several cracks can be seen radiating into the material bulk (arrowed), (Field width 500 µm). B: is an SEM of the same glass type, showing the fractured left margin (M) and lifted unsupported plates of cavo-surface glass (E). (Field width 2.5 mm).

FIG. 2-2 shows a sawn 58S monolith, showing marked tearing and scoring of the cut surface (S). Cavo-surface angle chipping is pronounced (E) and a fracture is evident, extending off into the bulk of the glass (#). The nearer edge of the slot is missing due to spontaneous fracture (F) from just behind the leading edge of the cut. (Field width ~1.5 mm).

FIG. 4-1 illustrates serial real-time confocal images of 45S5 Bioglass® being machined (rotary cut) at A: 0.5 mm/min, B: 1 mm/min, C: 2 mm/min & D: 4 mm/min. In A, there is little cracking and an absence of swarf. However, acceleration of the cutting immediately produced edge chipping (*) and fracture lines (#) began to radiate into the specimen bulk, leading to massive failures (X). Beyond 4 mm/min all specimens shattered. E: shows the remaining part of the same specimen, demonstrating the silicon laminae within the Bioglass® mass and fractures radiating from these planes into the material bulk. F: shows the view along the cut edge in E to the point of ultimate failure throughout the monolith, achieved in this specimen at 4 mm/min feed rate. (Field width approx. 1 mm in all cases, except E & F=2 mm).

FIG. 4-2 illustrates real-time Confocal imaging of rotary cutting of 58S bioactive glass monoliths at A: 0.5 mm/min, B: 1 mm/min, C:2 mm/min & D:4 mm/min. Swarf was produced well at the slower feed rates (S) but marginal failures (#) occurred at all bar the slowest speeds. Once established, they could not be cut past and fractures (F) radiated into the bulk of the substrate at higher speeds. (Field widths approx. 1 mm).

FIG. 4-3 illustrates a 58S glass fragment, cut at a maximum feed rate of 8 mm/min just prior to failure. A: showing smeared material over the remaining cut face (C) (Field width~2 mm). Detail of right hand margin B: showed crystalline deposits on the cut glass, confirmed by EDXA to contain high levels of Tungsten. The fracture plane revealed pore like structures (P) within the glass mass. (Field width~300 µm).

FIG. 7-1 illustrates air abrasive cutting (LtoR) of 45S5 bioactive glass A–E: ×40 serial real-time confocal images (at approximately 20 msec intervals) of the cutting front, demonstrating re-entrant fractures (arrowed) as the cutting mechanism (Field width~100 µm: ×40/0.55 na lens). F: SEM of cut surface, clearly showing re-entrant fractures at the cavo-surface angle (L) and the roughened, amorphous finish surface. No fractures were seen to radiate into the substrate, leaving a sound finished article (Field width 600 µm). G: High magnification view of the cut face, showing evidence of particulate cutting debris lodged in the cut face, some of which proved to be flakes of Bioglass® (X) and others, alumina (AL)—by EDXA. (Field width 300 µm).

FIG. 7-2 illustrates air abrasive cutting (RtoL) of 58S bioactive glass. A–E: Serial confocal real-time images of the cutting front at approximately 20 msec intervals, showing serial re-entrant fractures (arrowed) as the mechanism of substrate failure (×24/0.6 na "Hill" lens field width~200 µm) F: High magnification view of the finished cavo-surface angle, showing a well defined margin and the typical pitted, amorphous finish surface. The porous nature of the cut surface has been preserved, not being obstructed by cutting debris (Field width 250 µm) G: A low magnification view showing 100 µm sliver of glass being machined from the edge of a 58S monolith, without cracking in either monolith or cut wafer (Field width 2 mm).

Figure 1:
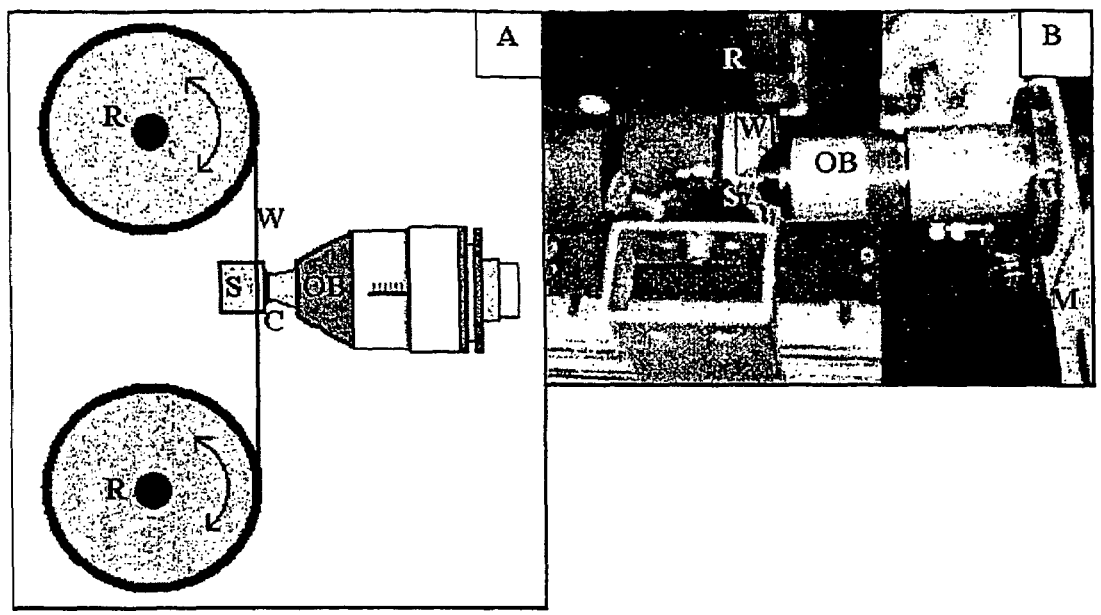
FIG. 1 illustrates a schematic of the set-up used in the wire saw cutting experiment, showing the diamond wire (W) reciprocally wound between reels (R). The specimen (S) is imaged using long working length internally focussed "Hill" type objectives (O) on a right-angled TSM confocal microscope (M), using a methylcellulose coupling agent (C). The same features are shown in B, the apparatus as set up for real time confocal subsurface saw cutting imaging.

The present invention is suitable for cutting and shaping any bioactive glass object. Such objects include but are not limited to medical and surgical implants for human and veterinary use, tissue engineering scaffolds, drug delivery depots and biosensors. The bioactive glass objects may be produced either by the melt process or the sol-gel process. The bioactive glass objects may be mixtures of more than one bioactive glass.

The term "cutting or cut" as used herein refers to any process whereby material is removed from the bioactive glass substrate, such as carving, shaping, trimming, refining, boring, drilling, finishing, shaving and shearing.

The use of propellant gases or gaseous mixtures other than air (e.g. $CO_2$ or $N_2$) is included in the definition of "air abrasion" as is the use of water or other fluids to act as propellants or as dust suppression agents—included in the gas stream or entrained around it (e.g. The Aquacut air abrasive machine—Medivance Instruments Ltd, Harlesden, London).

The term "bioactive glass" as used herein refers to a glass or ceramic or material of any particular form e.g. monolithic, foam or other scaffold formats, comprising Si-oxide or Si-hydroxide which is capable of developing a surface calcium phosphate/hydroxy-carbonate apatite layer in the presence of an aqueous medium, or at the interface of body tissues and the glass, so producing a biologically useful response.

Bioactive glass particles suitable for use with the present invention include the silicon based bioactive glasses derived from the Sol-Gel process (Hench L L., West J K., 1990, The Sol-gel Process, Chem. Reviews, 90, 33–72) or the Melt process (Hench L L., Wilson J., 1993 Introduction to Bioceramics. Publisher: World Scientific). Preferably the target bioactive glass object is derived from the Sol-Gel process.

Although it may be possible for a bioactive glass lacking a source of calcium or phosphorus to generate an apatite layer in vivo by utilising endogenous sources of these ions, typically a bioactive glass will comprise a source of at least one of calcium or phosphorous in addition to a source of Si-oxide or Si-hydroxide. Typically the bioactive glass will comprise a source of calcium. Optionally the bioactive glass may contain further hardening and/or softening agents. Such softening agents may be selected from: sodium, potassium, calcium, magnesium, boron, titanium, aluminum, nitrogen, phosphorous and fluoride. Additions of sodium, potassium, calcium and phosphorus are most commonly used, to reduce the melting temperature of the glass and to disrupt the Si networks within it. Optionally, hardening agents such as $TiO_2$ may be included in the glass composition. Its presence would allow crystallization to occur within its structure, so producing a glass-ceramic material, whose hardness will be greater than that of the glass alone. An example of a bioactive glass-ceramic material is Appatite/Wollastonite bioactive glass (see Hench L. L., 1998, Bioceramics The Centennial Feature, J. Am. Ceram. Soc., 81, 1705–1728).

Thus, composition ranges for bioactive glasses which may be used with the present invention are as follow:

| | |
|---|---|
| $SiO_2$ or $Si(OH)_2$ | 1–100% |
| CaO | 0–60% |
| $P_2O_5$ | 0–60% |
| $Na_2O$ | 0–45% |
| $K_2O$ | 0–45% |
| MgO | 0–40% |

Plus additions of Na, K, Ca, Mg, B, Ti, Al, P, N and F as necessary.

The product glasses may contain purely Si/Si gel compounds, or may comprise two or more of these phases, one of which will be Si/Si gel based (Bi & tri phasic sol-gel glasses being most commonly used, whereas melt derived glasses tend to be ternay systems).

Preferably, a bioactive glass will contain between 30 and 100% Si-oxide or Si-hydroxide, more preferably between 40 and 85%.

In a further preferred embodiment the bioactive glass will contain between 5 and 60% Ca, more preferably between 30 and 55%.

With respect to a source of phosphorus, the bioactive glass will contain between 5 and 40% P, more preferably between 10 and 30%.

Thus, in one embodiment the bioactive glass particles will comprise $SiO_2$, CaO and $P_2O_5$. Preferably the bioactive glass includes from 44 to 86 weight % $SiO_2$, from 4 to 46 weight % CaO and from 3 to 15 weight % $P_2O_5$. Preferably the bioactive glass is prepared by the sol gel route and comprises from 55 to 86 weight % $SiO_2$, from 4 to 33 weight % CaO and from 3 to 15 weight % $P_2O_5$. Preferably such a bioactive glass has the composition 58 weight % $SiO_2$, 33 weight % CaO and 9 weight % $P_2O_5$.

In an alternative embodiment the bioactive glass particles may be prepared by the Melt method such as that described in U.S. Pat. No. 5,981,412. Such a glass may have a composition of from 40 to 51 weight % $SiO_2$, 23 to 25 weight % CaO, 23 to 25 weight % $Na_2O$ and 0 to 6 weight % $P_2O_5$. Preferably such a bioactive glass has the composition (by weight);

$SiO_2$—45%
$NaO_2$—24.5%
CaO—24.5%
$P_2O_5$—6%.

Such a bioactive glass is available commercially as Bioglass® 45S5.

The manufacturing and processing methods used in the silicon based bioactive glass family are ideally suited to the production of tailored particles for cutting bioactive glass objects of different strengths and hardnesses.

As mentioned above, hardening and softening components may be added to modulate the hardness of the bioactive glass particles and hence control the cutting action according to the nature of the object glass they are intended to cut. While accepting other known air abrasion cutting variables such as particle size, morphology and speed, the greater the difference in hardness between the glass of the object and the glass of the abrasive particles the easier and more efficient the cutting process. In contrast, the smaller the difference in hardness between the glass of the object and the glass of the abrasive particles the slower and more controllable the cutting process. Thus, either by selecting from known bioactive glasses or by varying the amounts of hardening and/or softening agents present in the abrasive glass particles the skilled man will be able to prepare bioactive glass air abrasive agents capable of cutting a particular glass object.

Similarly, by controlling the processing conditions in the densification phase of the sol gel process (Hench L L., West J K., 1990, The Sol-gel Process, Chem. Reviews, 90, 33–72. Hench L L., West J K., 1996, Biological applications of Bioactive glasses, Life Chemistry Reports, 13, 187–241.) sol-gel variants of bioactive glasses can be processed to differing densities and ultimate strengths and hardnesses.

Vickers Hardness values for exemplary glasses are shown in Table 1. A well densified 58S sol-gel Bioglass specimen yielded a Vickers Hardness of approximately 110 (less densified specimens have lower hardnesses) compared with alumina 2,300.

Preferably the abrasive glass particles are at least as hard as that of the glass in the object they are intended to cut.

TABLE 1

| | Vicker's Hardness Numbers. |
|---|---|
| Alumina | 2000–2300 |
| Glass beads | 500–550 |
| Crushed glass powder | 500–550 |
| Bioglass ® 45S5 | 458 +/− 9.4 |
| Appatite/Wollastonite bioactive glass-ceramic | 680 |
| 58S Sol-gel bioactive glass (fully densified) | 110 |

Figure 11:
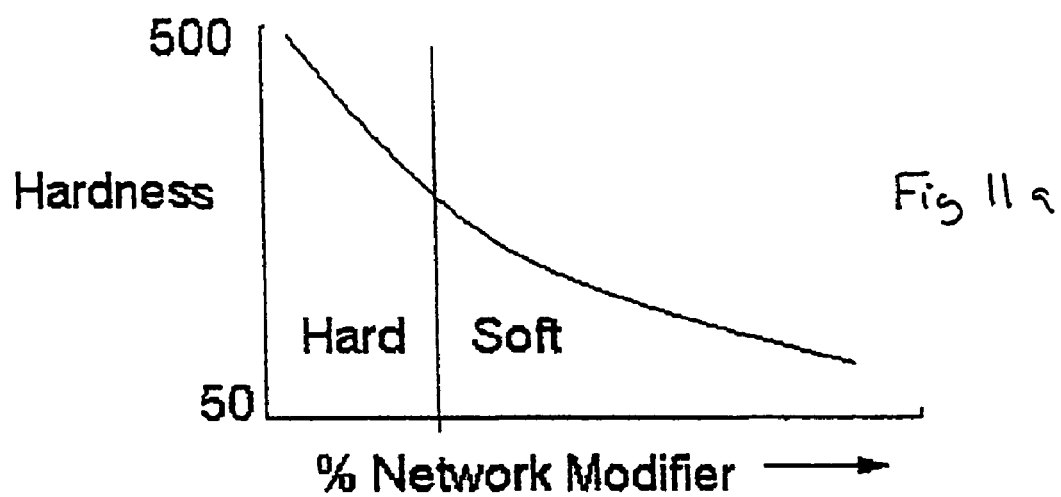
FIGS. 11a and 11b show the effect of network modifiers (hardening and softening agents) and density on glass hardness.
Figure 11:
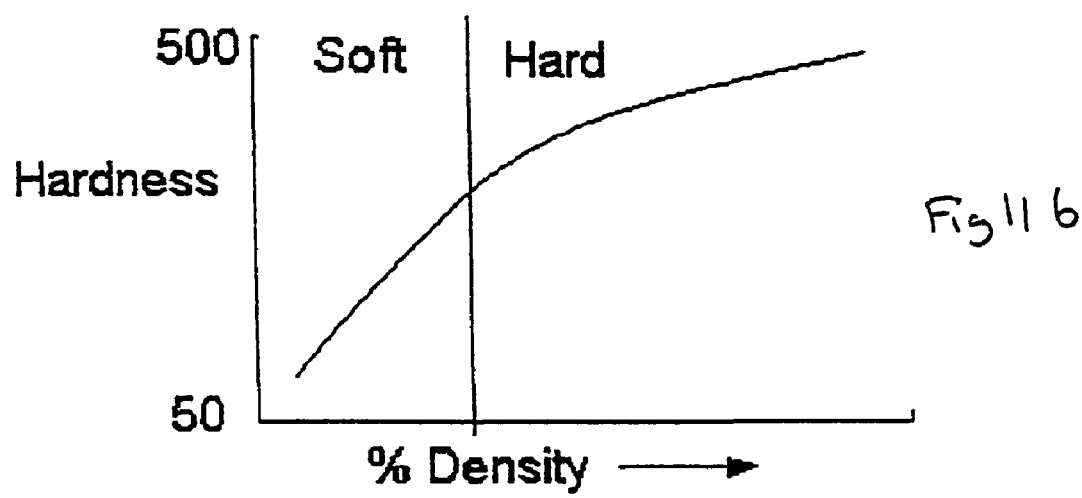

By increasing the quantity of network modifier (non-silica species, e.g. Na, K, Ca, Mn, Br, Al, N, P, Fl etc) the hardness of the finished glass decreases. (see FIG. 11a). These modifiers may be added to the melt derived glasses while in their molten states, or to sol-gel materials at the mixing phase of production. Hardness may also be decreased by increasing the porosity within the sol-gel glass, achieved by variations in the drying and stabilisation and densification phases of their production. As described above, the hardness of glasses can be increased by allowing crystal formation within them, so the use of $TiO_2$ can act as a hardening agent, as the glass becomes a glass ceramic. Also modifications to the sol-gel processing phases allowing a more dense glass product will result in a harder product (see FIG. 11b).

A further consideration when preparing a bioactive glass for use in the present invention is the size and shape of the bioactive glass particles. These may be selected depending on the intended application. Angular particles are better suited to cutting quickly through hard materials whereas rounded particles are more suited to cutting softer materials or cutting intricate and precise shapes. The shape of bioactive glass particles may be controlled by selecting the appropriate particulation process from, for example, grinding, crushing or air-collision milling during their manufacture. Thus, crushing produces sharper angulated particles, whereas, air collision milling will produce more rounded particles. Grinding (e.g. ball milling) however, will produce particles of a more intermediate shape. Size selection can be achieved with routine sieving processes. These processes are suitable for glasses produced by both the sol-gel and melt routes.

Particles most suitable for use in the present invention will have a diameter in the range of 1 µm to 1 mm, more preferably in the range of 10 µm to 500 µpm.

In cutting a particular object one or more glasses may be employed to cut or shape the object as required.

The present invention may be used with conventional air abrasion systems well known to those skilled in the art. Examples of suitable air abrasion systems include the Velopex® Alycat marketed by Medivance Instruments Ltd., which permits switching the source of the abrasive agent during cutting operations.

It is to be understood that the present invention covers all combinations of suitable and preferred groups described hereinabove.

The present invention will now be illustrated, but is not intended to be limited, by means of the following examples.

General

Three separate apparatus were developed and constructed to allow real time imaging and comparison of rotary, linear and air abrasive cutting of bioactive glasses. Each method is described in turn, to which, five specimens of each material test type were submitted. The materials examined comprised: 45S5 melt derived Bioglass® objects and 58S sol-gel bioactive glass objects. All material specimens were of a uniform 5 mm×5 mm×3 mm deep slab format except in wire saw investigations, where 8 mm deep slabs were used.

Wire Saw Cutting

Apparatus

The experiments aimed to examine linear saw cutting into the specimen types, using real-time confocal microscopic imaging of the cutting processes and scanning electron microscopic (SEM) examination of the residual finished surfaces and margins. A schematic of the experimental set-up is shown in FIG. 1. The diamond wire saw chosen for the study was that considered to be the most "gentle" available within the laboratory. A reciprocating diamond wire saw, (Precision Wire Saw:—Well 3241-2 Bennetech, Leicester, UK) specifically designed to section brittle crystalline materials such as human dentine and enamel. The saw comprises a fine (approximately 100 µm grit) diamond encrusted stainless steel wire, 300 µm diameter & 10 m long. The wire is wound from upper to lower reel and back again, providing the reciprocating action. The minimum wire velocity of 0.1 m/sec was found to be necessary to avoid binding or stalling during each pass.

Specimens were held in position on the saw's mounting bracket using command cured dental composite materials (Coltene SE Composite, Coltene Whaledent Dentalvertriebs Gmbh, Konstanz, Germany) and thermoplastic dental composition (Kerr, Romulus, Mich., USA). Each slab specimen (5 mm×5 min 8 mm deep) was held with one of its short axes parallel to the line of the wire saw and using the micrometer positioning device, the initial saw cut was guided to the centre of the 8 mm deep specimen face offered to the diamond encrusted wire.

The reciprocating saw machinery was mounted on a cradle on gravity runway, whose inclination was adjusted to give an applied cutting load of 10 g—the minimum to ensure free travel of the cradle while keeping the active wire in constant contact with the substrate. Once aligned with wire saw and a minimal engaging cut started, the complete saw assembly (mounted on a wheeled trolley) was then brought alongside the Tandem Scanning Confocal Reflected Light Microscope—TSM (Koran, Madison, Wis., USA) employed in the study. The illumination for the experiments was derived from a 100W mercury arc lamp. This instrument had previously been modified for side viewing, allowing in vivo imaging of dental restorations using "Hill" type ultra long working length (8 MM) internally focussing lenses (Petroll W., Cavanagh H., Jester J., Scanning, 1991, vol. 13, I-92 and I-93).

The mounting cradle had been earlier adjusted to deliver mounted glass specimens to the level of the side-viewing lens. As the saw action was totally encased within the glass specimen, it was less critical to achieve an absolutely optically flat surface, perpendicular to the optical axis of the objective lens. Methylcellulose gel (K-Y Jelly. J&J Healthcare, UK) optically coupled the lens to the specimen, further reducing the interface surface reflection interference. With gentle repositioning of the saw machinery and fine adjustments undertaken using the lens' own remotely driven internal focus systems (Petroll W., Cavanagh H., Jester J., Scanning, 1991, vol. 13, I-92 and I-93), dynamic imaging of the wire saw during cutting was possible, image capture being undertaken using a low light level SIT (Silicon Intensified Target) camera (JAI, Copenhagen, Denmark.), recording to S-VHS videotape. Real-time sequences (25 frames per second) of particular note and specific frames of interest were later converted to digital format, using a Studio MP10 converter (Pinnacle Systems, Calif., USA).

Short video sequences of cutting were found to be recordable, only in the more translucent specimens. The opacity of the 58S glass defeated the confocal system and video imaging was not possible with so little contrast from such high-speed events at any significant depth within the sol-gel glass substrate. Real-time in-situ images were therefore only recorded for the clear 45S5 bioactive glass materials. All cut specimens were however retained for SEM imaging and cut surface/edge analysis and interpretation afterwards.

Results

Figures 1, 2:
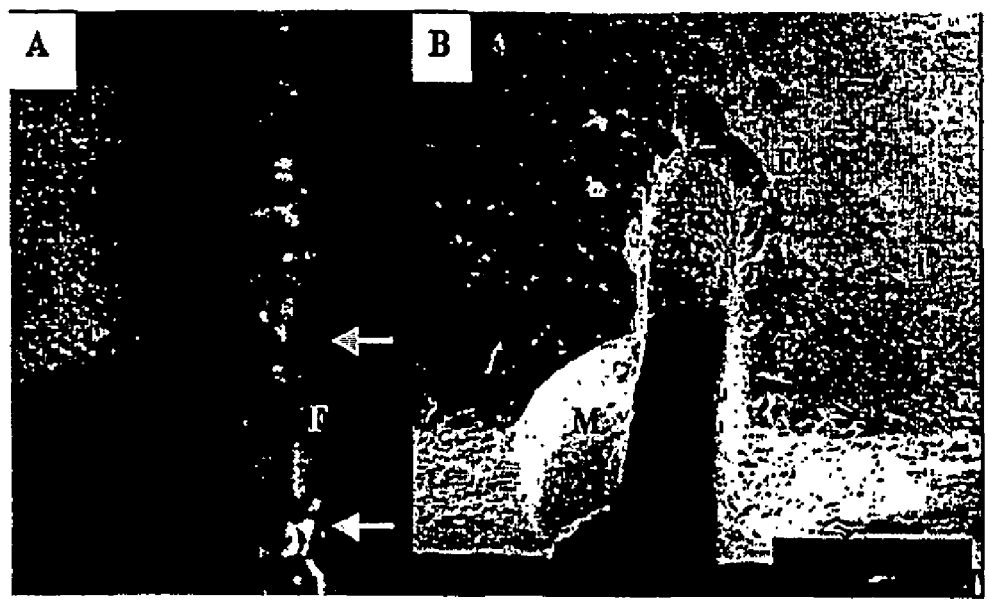
Figure 2:

45S5 Bioactive Glass—(FIG. 2-1)

Being reasonably hard and brittle, 45S5 Bioglass® displayed both chipping and fracture processes both superficially and deep within the bulk of the saw cut itself, during each cutting stroke. The images from both SEM and real-time confocal imaging, showed evidence of similar fracture—failure cutting patterns, the leading edge of the glass being particularly vulnerable to cracks extending at least a short way into the mass of the material. If close to a second surface, substrate failure would occur, the crack propagating toward that surface. Typically one marginal wall would fracture out to the bulk's surface or unsupported cavosurface angles and edges failed, plates of superficial glass lifting at the cavo-surface margins.

The size of fractured plates of glass lifted from the cavo-surface angle was of the order of 100 μm diameter each. Furthermore, it proved impossible to identify the saw blade's pattern of movement in this material as no evidence of slumping or thermoplastic behaviour was discernable from the scored and cracked finish surface patterns.

The findings reflect the interaction of a hard brittle substrate with the individual diamond crystals of the fine wire saw, little of the residual surface morphology being attributable to thermally generated fracture.

58S Sol-Gel Bioactive Glass—(FIG. 2-2)

The 58S bioactive glass specimens frequently suffered catastrophic failure, large pieces (several millimeters wide) fracturing away from the sawn line. Fractures radiated off from the saw path and unsupported cavo-surface edges were also prone to localised chipping and fracture too. The sawn surface showed deep, ragged, gouges and striations, similar to that seen in the 45S5 specimens. Similarly, the direction of the wire saw's movement could not be positively interpreted from the SEM images.

The substrate bulk fractures, often arose from the greatest depths of the sawn slot, giving the impression that even if seemingly sound at the end of a cutting phase, the specimen was likely to be fundamentally flawed and weakened. Indeed in some specimens the failures occurred spontaneously from within the bulk of the substrate. Although confocal imaging was not possible, the similarity of 58S and 45S5 glass SEM images and their concordance with the confocal real-time images showing fractures extending off into the cut substrate bulk, supports the assertion that similar behaviour is occurring in both of these bioactive glasses.

Thus, glass substrate fracture was commonly seen for both the sol and melt derived glasses. Thus wire saw cutting is inappropriate for cutting and shaping bioactive glass objects shaping.

Rotary Cutting

Apparatus

Figure 3:
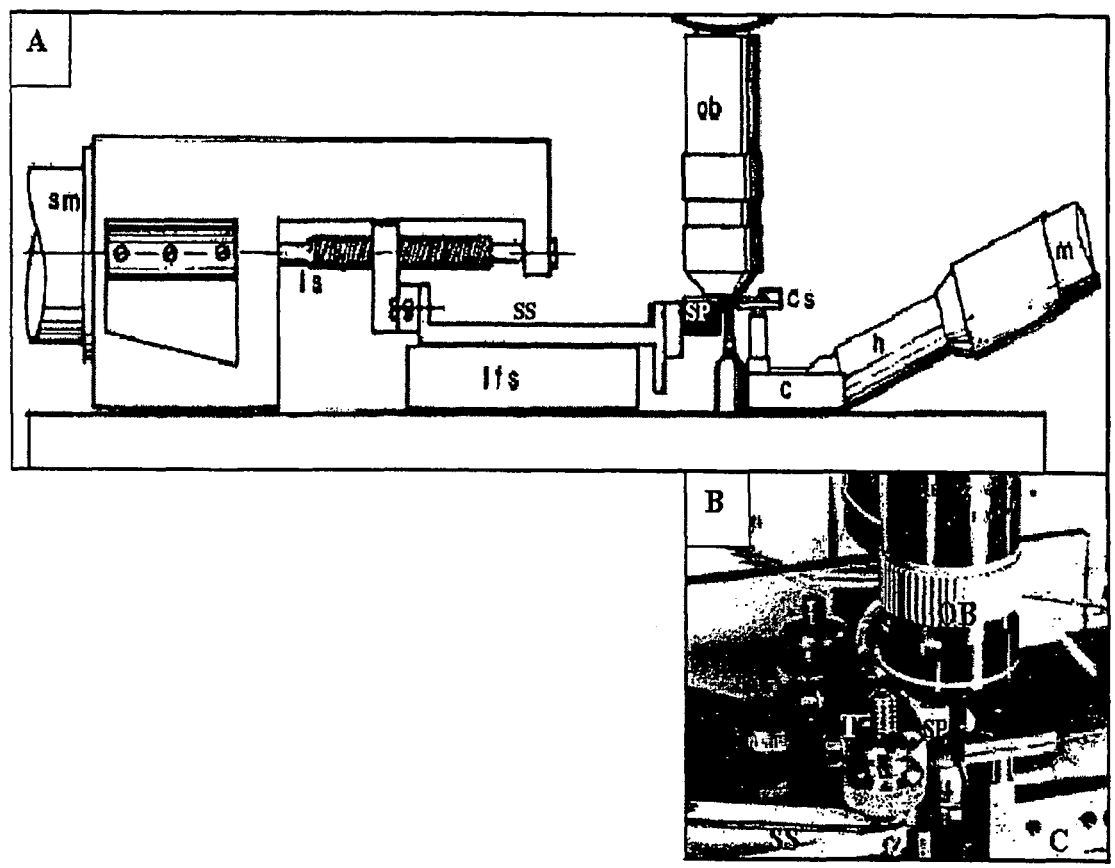
FIG. 3 illustrates a schematic of the rotary cutting set-up, showing stepper motor (SM) driving the specimen support stage (SS), through a lead screw (LS). The support stage, carried on linear ball races, drove the specimens (SP), aligned with a tripod sub assembly (T) onto the rotating bur (B), driven by a step up handpiece (H) (200 kRPM) by motor (M). The confocal microscope's objective lens (OB) was protected by cover slip (CS) from the slot cutting events just beneath. B: shows a close up image of the specimen carriage (SS) with its sample (optical plane) adjusting mechanisms, the confocal microscope's objective lens (OB) and the handpiece supporting cradle (C).

A precision sliding carriage microscope sub-stage, originally designed and constructed for dental cutting experiments (Watson T., Flannagan D., Stone D., B.D.J., 2000, vol. 157, p 680–686, Watson T., Cook R., 1995, J. Dent. Res., 74, 1749–1755 and Watson T., 1990, J. Microsc., vol. 157, p 51–60) was adapted to allow imaging of the rotary cutting of glass materials. A schematic of the experimental setup is shown in FIG. 3. Test specimens, mounted on a bespoke jig, using light cured dental composite resin as an auto-casting, command set rigid support medium (Coltene SE Composite, Coltene Whaledent, Dentalvertriebs Gmbh, Konstanz, Germany), were introduced to a rotating cutting bur whose long axis was aligned with the conventional vertical optical axis of a Tandem Scanning Confocal Reflected Light Microscope—the TSM (Noran, Madison, Wis., USA) with 100W mercury arc illumination and long working range objective lenses.

Using a glass coverslip as a guide, the upper surface of the experimental materials were contrived to be par-focal with the end cutting flutes of the bur and were held in an optically flat plane, judged by the phenomenon of chromatic aberration (Watson T., 1997, Adv. Dent. Res., vol. 11, p 433–441 and Watson T., Cook R., 1995, J. Dent. Res., 74, 1749–1755).

The specimen support jig was itself bolted to an intermediate tripod frame on the specimen carriage, allowing adjustment of the specimen's upper surface in three planes. Although viewing sub surface events during the cutting to avoid inclusion of erroneous unsupported surface failure patterns, it was essential that the specimen be held level with the cutting bur end, to avoid confusing side-cutting events with the problematical phenomena of end cutting (Watson T., Cook R., 1995, J. Dent. Res., 74, 1749–1755).

It is well accepted that the more concentric a rotary cutting instrument, the less heat, vibration and unwanted side effects will arise during cutting (Watson T., Cook R., 1995, J. Dent. Res., 74, 1749–1755). For this reason, the crystalline irregularities of diamond burs were rejected in favour of the most concentric (i.e. one-piece engineered, non cross cut fissure pattern) tungsten carbide burs available ("Smartburs" Precision Rotary Instruments Inc, Bridgewater Corners, Vt., USA) (Watson T., Cook R., 1995, J. Dent. Res., 74, 1749–1755). This particular brand had previously been demonstrated to have significant advantages over typical two part (T.C. head sintered to steel shank) burs, especially in the condition of residual substrate when cutting hard, brittle materials (Watson T., Flannagan D., Stone D., B.D.J., 2000, vol. 157, p 680–686, Watson T., Cook R., 1995, J. Dent. Res., 74, 1749–1755). A Fresh bur was made available for each cutting action in each specimen group, so making the comparison as fair as possible.

Thus, real time confocal reflected light imaging of the substrate's structure being cut, was achieved (Watson T., Flannagan D., Stone D., B.D.J., 2000, vol. 157, p 680–686, Watson T., Cook R., 1995, J. Dent. Res., 74, 1749–1755 and Watson T., 1990, J. Microsc., vol. 157, p 51–60). The long axis of the rotating bur did not change during each pass, allowing the point of cutting to be imaged throughout individual experiments, as the specimen was carried forwards onto the rotary bur by a calibrated, stepper motor driven lead screw. Thus effectively, a slot machining process was imaged in real time, the advance rate of the specimen being known and recorded throughout the procedure (0.5–8 mm/min advance rate range). The images were captured using a cooled Charged Coupled Device (CCD) monochrome camera (Cohu), through the confocal microscope's imaging port, and were stored on S-VHS video tape for later analysis. An audio commentary provided synchronised cutting speed/time data during playback.

All rotary cut specimens were imaged during their cutting, and the specimens were retrieved afterwards, being submitted for SEM examination of their cut surfaces and edges. Where substrates failed, the fragments were collected as best possible, and were nonetheless submitted for SEM examination.

Results.

Figures 1, 4:
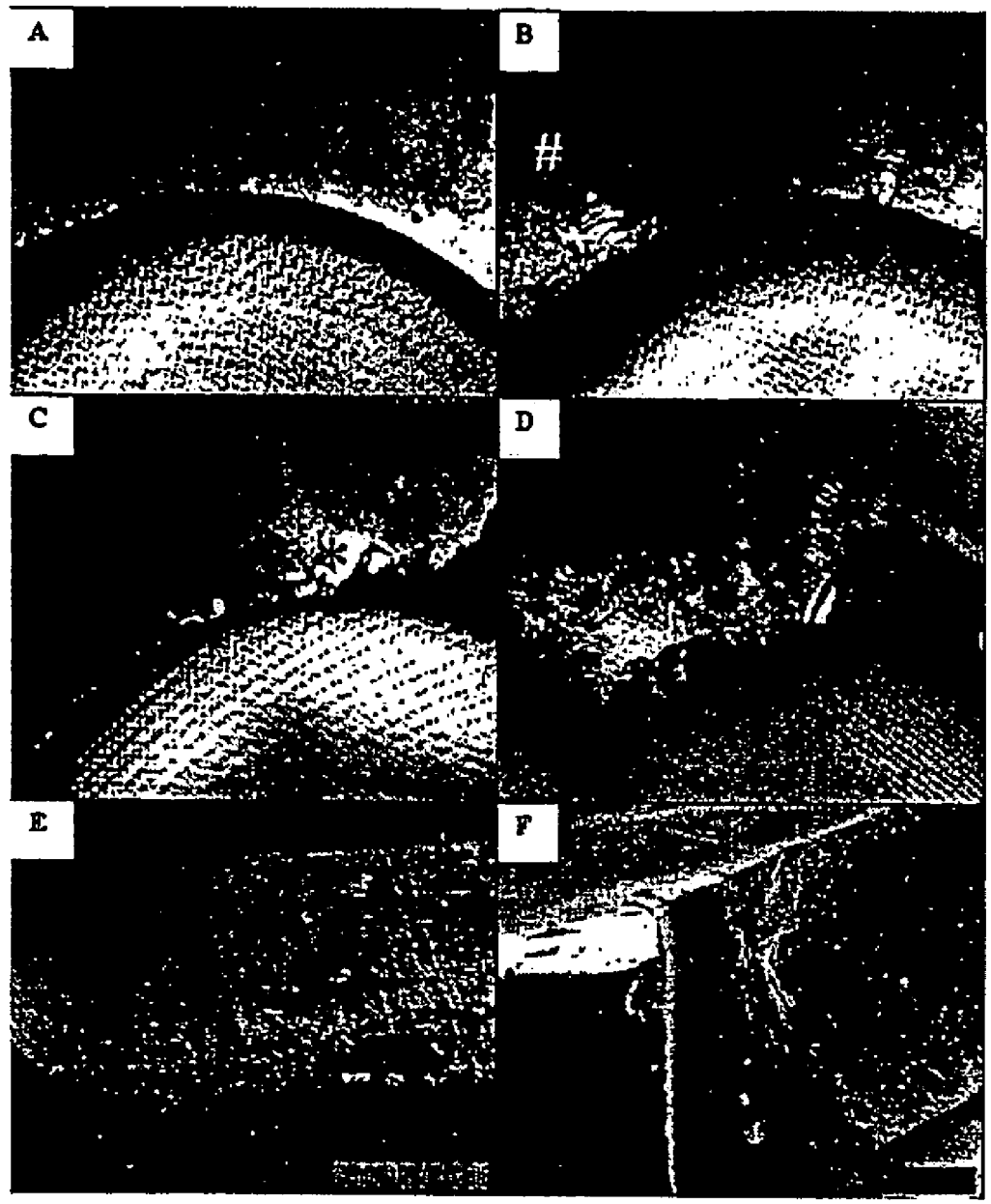
Figures 2, 4:
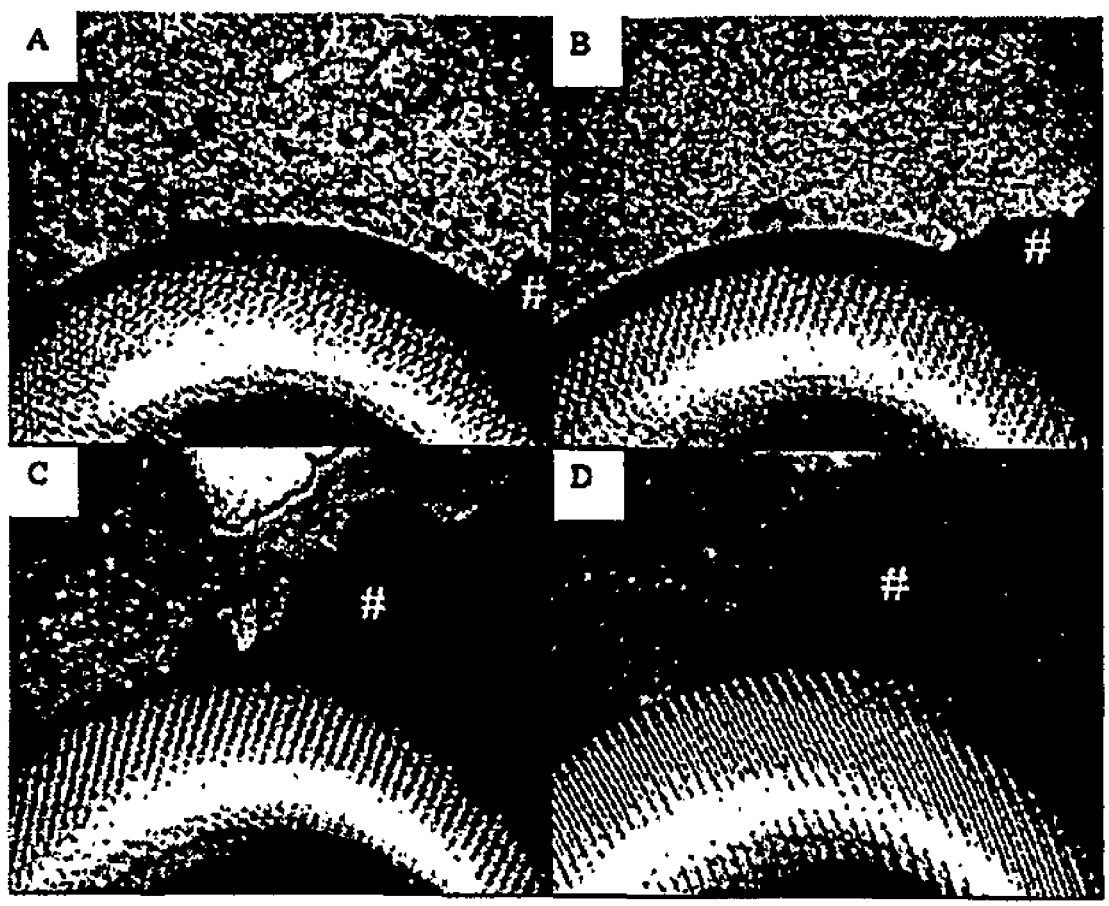
Figures 3, 4:

45S5 Bioglass®—(FIG. 4-1)

During each experiment on each Bioglass monolith, fracture of the substrate was always seen both local to the cutting process itself and radiating off into the bulk of the substrate. Even at the minimal feed rate of 0.5–1 mm/minute, spontaneous fractures were seen to propagate into the substrate mass. The poor cutting was matched by a poor swarf production. Those few particles seen to develop, appeared as small splinters rather than aggregated material often seen in the cutting of machineable borosilicate glasses.

At any appreciable cutting rate, the Bioglass® structure failed en mass. Retrieved sections—usually the better supported entry side (left side in the real time cutting images, as the bur rotated clockwise from the viewing perspective)—showed no evidence of rippling and at no time was bur uprighting seen, implying that there was minimal vibration in the cutting system. However, examination of the cut surfaces revealed the shattered edges of the silicon laminae, individually failing and producing a series of steps in the Bioglass® finish surface.

58S Sol-Gel Bioactive Glass—(FIGS. 4-2 & 4-3)

The sol-gel specimens behaved very differently to melt derived glasses when subjected to rotary cutting. At very slow feed rates (0.5 mm/min) a good aggregated swarf was produced (resembling that of the machineable borosilicate glasses, in shape and production rate), but on the unsupported exit side of the machined slot, substrate failure was regularly seen. At slow advance speeds (up to 1 mm/min) the failure appeared as localised fracture or "crumbling" of the marginal glass: Once established, an exit side failure could not be cut past i.e. as the bur approached the deepest extent of the previous failure, rather than establish a new slot margin, further exit side collapse would preferentially occur, perpetuating the cycle. At higher feed rates, the exit side failure pattern was perpetuated but the fragments lost were larger at each event, reflecting a greater energy input at higher cutting speeds. Beyond 4 mm/min, all specimens shattered and were lost, only small fragments remaining. Examination of an entry side fragment clearly showed multiple fractures radiating into the substrate from the cut surface. Fractures were not seen on this side during the real-time imaging of the cutting events, as the bulk material was self-supporting on the entry side. It was noted that just prior to failure, pale incandescence was visible from some of the specimens, accompanied by a deterioration in the contrast of the confocal cutting image, caused by additional light entering the confocal system, generated from within the optical focal plane itself.

This alone indicated an excessive amount of heat being generated at the cutting interface, enough to cause transfer of tungsten metal crystals from bur to substrate surface (confirmed on SEM examination of the residual cut glass specimens) Bearing in mind the fragility of the bioactive reaction, such adulteration of the cut glass surface is unacceptable for both experimental and medical use.

Examination of the Tungsten carbide Smartburs after machining one 5 mm slot in a single 58S monolith revealed the amount of wear induced in this one cutting action. The transfer of metal to the residual substrate and the loss of all its sharp working surfaces and edge profiles, providing further evidence of the enormous heat and abrasive damage experienced during a single cutting process.

Thus, rotary cutting is hopeless for any shaping process for sol-gel glasses, while only the most superficial trimming of surfaces of large monoliths of 45S5 glass may be practical. Any fine surface detail will not survive, despite using the most concentric cutting instruments available (Watson T., Cook R., 1995, J. Dent. Res., 74, 1749–1755).

Alumina Air Abrasion Cutting

Apparatus

Figure 5:
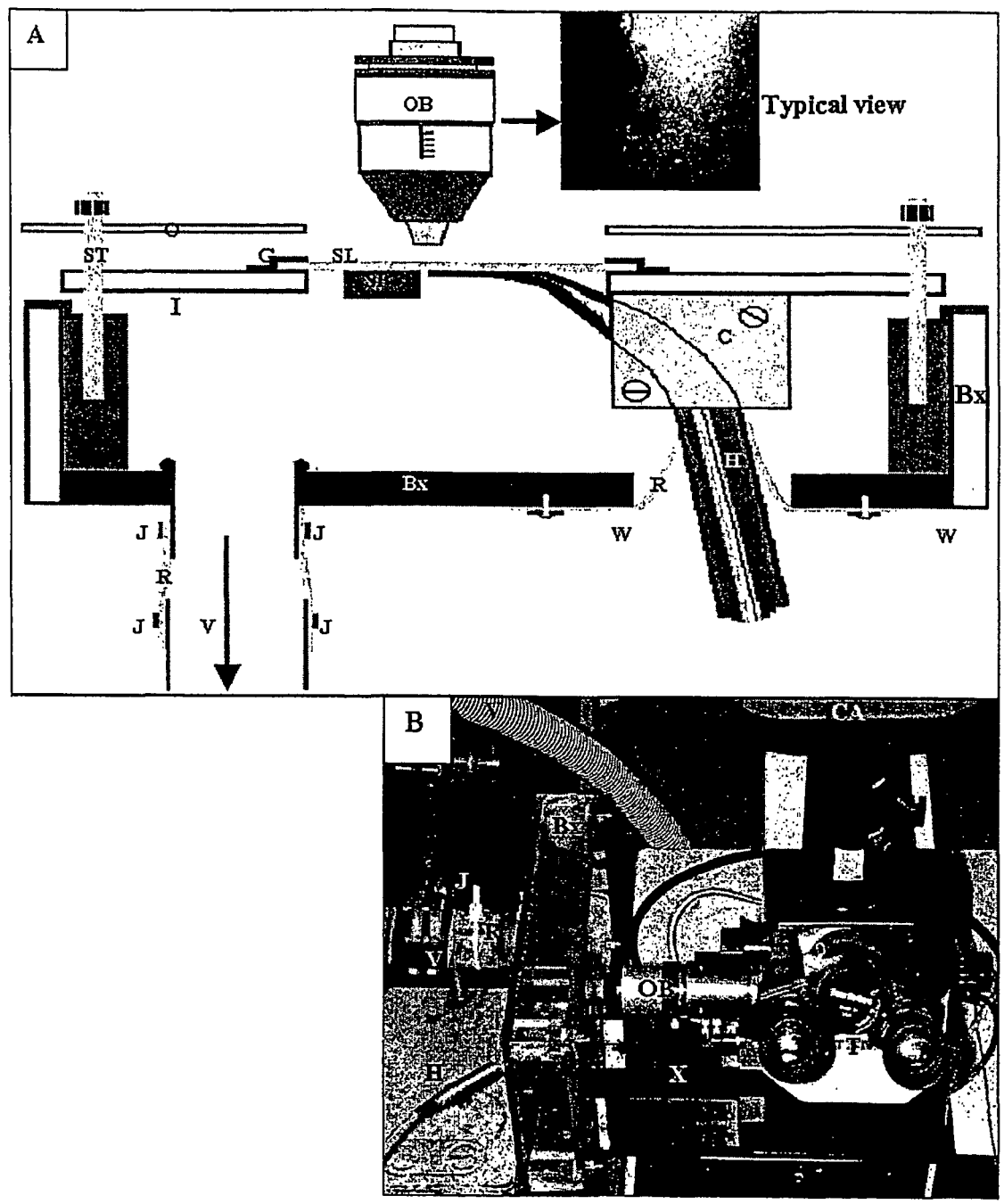
FIG. 5 illustrates a schematic of the air abrasion set-up for confocal imaging, showing outer lid (O) clamping the mounting slide (SL) and specimen (SP) against the inner lid (I) and main structure of the box (Bx), using 3BA brass studding (ST) set into the corner pillars. Bespoke gaskets (G) were made from dental silicone impression material. Rubber sheet (R) provided a flexible seal with minimum vibration transmission, for both the air abrader handpiece (H), clamped (C) within the dust chamber and also the vacuum outlet (V). These seals were retained by either Jubilee type plastic clips (J), or a screw retained tapped steel washer (W). The Hill type internal focussing long working length objective lens (OB) confocally imaged sub-surface cutting sequences, focussing through the glass mounting slide and clear adhesive. A typical image is shown as an insert in part A. Part B shows the set-up mounted on the especially extended stage (X) of the side viewing TSM (T)—hence "X" stage movement became the coarse focus. The cutting events were recorded via a JAI SIT camera (CA), recording to S-VHS video tape (Cook R. J., Azzopardi A., Thompson I. D., Watson T. F., 2001, J. Microsc., 203, 199–207).

A schematic of the experimental setup is shown in FIG. 5. The apparatus design (Cook R. J., Azzopardi A., Thompson I. D., Watson T. F., 2001, The cutting Edge of Air Abrasion. Procs Far East Asia Second Symposium on Confocal Microscopy Sun-Yat Sen University, Taiwan. In Press and Cook R. J., Azzopardi A., Thompson I. D., Watson T. F., 2001, J. Microsc., 203, 199–207) comprised a rigid dust containment chamber, whose internal pressure was maintained below that of atmosphere by entraining air through all breaches in the walls' integrity, thereby minimising abrasive escape. The partial vacuum and unidirectional airflow was maintained using the commercial dust handling vacuum cleaner, supplied with the Lares air abrasion cutting unit employed (Lares Industries, California, USA).

The basic chamber consisted of a simple box: 20×35×5 cm constructed from sawn 5 mm thick sheet Perspex®. All joints were cemented using chloroform as a solvent and the corners were internally reinforced with 2×1 cm Perspex® pillars, rebated to allow the internally fitting first lid to rest on their upper surface and remain a flush fit with the walls. The lid, drilled to match, was retained using brass nuts on captured 3BA thread brass studding, set permanently in the axially drilled pillars, using a dissolved Perspex®/chloroform slurry.

The baseplate was drilled to allow access for the vacuum coupling, made from a spare 35 mm photographic film plastic container. To minimize transmitted vibrations from the vacuum apparatus via its hose, a soft flexible connector was produced to bridge the gap, by folding a sheet of dental rubber dam into a cylinder and securing it to both the chamber outlet and the vacuum hose, with "Jubilee" type clips.

Under test vacuum, the lid was found to flex, so Perspex legs were fitted, providing central support. Similarly, a rigid holding clamp was constructed for the air abrader handpiece within the cell. The air abrader hand-piece access hole was closed using a gasket of dental "Rubber dam," retained by a large steel "O" washer, tapped peripherally. The flexible sheet allowed adjustment of the hand-piece position within the cell, while maintaining a dust-tight seal.

In service, it was found that several 5 mm sidewall access holes (allowing screwdriver access for internal adjustments) were well tolerated by the system. Despite air abrasion inflow pressures of up to 100 psi, a relative internal vacuum, approximately 5–7 mmHg less than atmosphere, was successfully maintained, as the inflow volumes were relatively low.

The inner lid had a centrally cut access window, with dimensions 4 mm smaller than a standard microscope slide, so allowing mounting of the specimens within the chamber, and alignment of the air abrader nozzle 3 mm away from and perpendicular to the facing surface of the specimen. The glass microscope slide, to which the specimens were adhered, using the thinnest possible film of low viscosity clear cyanoacrylate impact adhesive (Watson T., Pilecki P., 1999, Procs. RMS, vol. 34. pp 485–487) was held in place by a second outer lid of 3 mm clear polycarbonate sheet, clamped by the corner fixing brass stud/nuts described above. To allow imaging, this too had a central viewing window matching that of the inner lid. To hold the specimen preparation in place and ensure a seal close to the optics, addition cured silicone dental impression materials (Aquasil, Dentsply DeTrey GmbH, Germany) were sparingly placed at the lid margins, producing bespoke gaskets.

The design thus allowed viewing of each specimen through a fresh glass window and the flexible hand-piece seal allowed re-alignments and several cutting attempts from each of the five specimens of each material group. During higher power confocal imaging, it was found useful to flat polish the air abrader head, allowing the nozzle orifice to come within 1 mm of the glass to maximise the depth of focus into the cut area of the substrate.

The chamber was securely bolted to an "X" axis extension platform fabricated to fit the conventional "X-Y" stage. Therefore, the stage controls were reassigned, the conventional "X" became the coarse "Z" focus, "Y" became the new "X" and the original "Z" became "Y". This adaptation though not essential, allowed handpiece and vacuum access through the baseplate (See FIG. 5). Fine focus was achieved using internally focussing long working length, "Hill" pattern (Petroll et al 1991) objective lenses: ×16/0.45 nd, ×24/0.6 nd (Tandem Scanning Corp. Annapolis, Md., USA) and a dry ×40/0.55 na lens (Nikon, Japan). Specimen imaging through the microscope slide and low viscosity clear cyanoacrylate impact adhesive was therefore straightforward. Prior to being mounted, specimens not having a finished flat surface were hand polished to P1200 grit, so minimising the adhesive interface depth, as trials had shown superior imaging of internal cutting events by this method.

All cutting experiments were undertaken using the same Lares (Lares Industries, California, USA) air abrasion machine incorporating a 600 µm diameter cutting nozzle, 27 µm diameter alumina cutting particulate and an instrument acceleration pressure setting of 80 psi. The same initial target to nozzle separation of 3 mm was also maintained throughout, allowing direct comparison of results, although imaging was from different depths within the specimens. Likewise, the same 'medium' powder flow rate (0.01 g/sec) was employed throughout.

To allow real time direct reflection imaging of the cutting interactions, a Tandem Scanning confocal Microscope—TSM (Noran, Madison, Wis., USA) was employed with 100W mercury arc illumination. This instrument had previously been modified for side viewing, allowing in vivo imaging of dental restorations. Image capture was undertaken using a low light level SIT (silicon intensified target) camera (JAI, Copenhagen, Denmark.), recording to S-VHS videotape. Real time sequences of particular note were later converted to digital format, using a Studio MP10 converter (Pinnacle Systems, California, USA), also allowing abstraction of specific frames of interest for illustrative purposes.

Cutting was thus imaged in real time, but little SEM evidence was possible unless the cyanoacrylate adhesive interface could be persuaded to fail at the end of the cutting run. Even so, the upper surfaces of the specimens were often found to have an adhesive coating, masking possible fractures or features within the specimen material beneath. Furthermore, any surface irregularities found, could have arisen from the de-bonding process.

Figure 6:
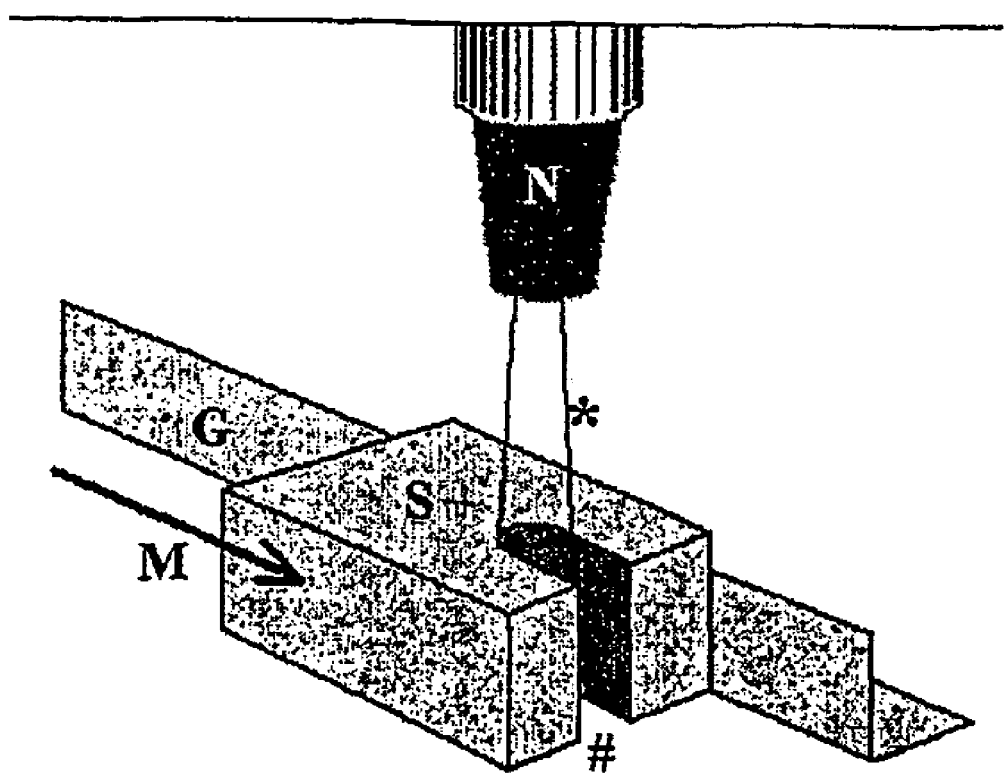
FIG. 6 illustrates a schematic diagram showing the air abrasion machining of slots (#) in substrates (S). The air abrasion nozzle (N) was held in a constant vertical relationship, 3 mm from the upper surface of the specimen, allowing the abrasive stream (*) to cut a slot in the passing substrate, moved (M) by hand along the metal guide (G).

Consequently, a final group of specimens were subjected to air abrasive cutting of a slot, machined in the same orientation as employed in the rotary and linear cutting work. A schematic of this experimental setup is shown in FIG. 6. The specimen was held flat on the floor of a commercial abrasive containment chamber (Handler, USA) and a slot was machined vertically downwards through the glass slabs, using a contrived jig/rest to maintain a constant nozzle—target distance of three millimeters as above. Machining a linear slot was achieved by moving the glass slab along a straight metal edge within the dust hood, passing the glass beneath the vertically orientated air abrasive nozzle. The same acceleration Pressure (80 psi), powder flow rate (0.01 g/sec) and the same 27 µm alumina particle diameter was maintained throughout, allowing direct comparison of results.

Results

Figures 1, 7:
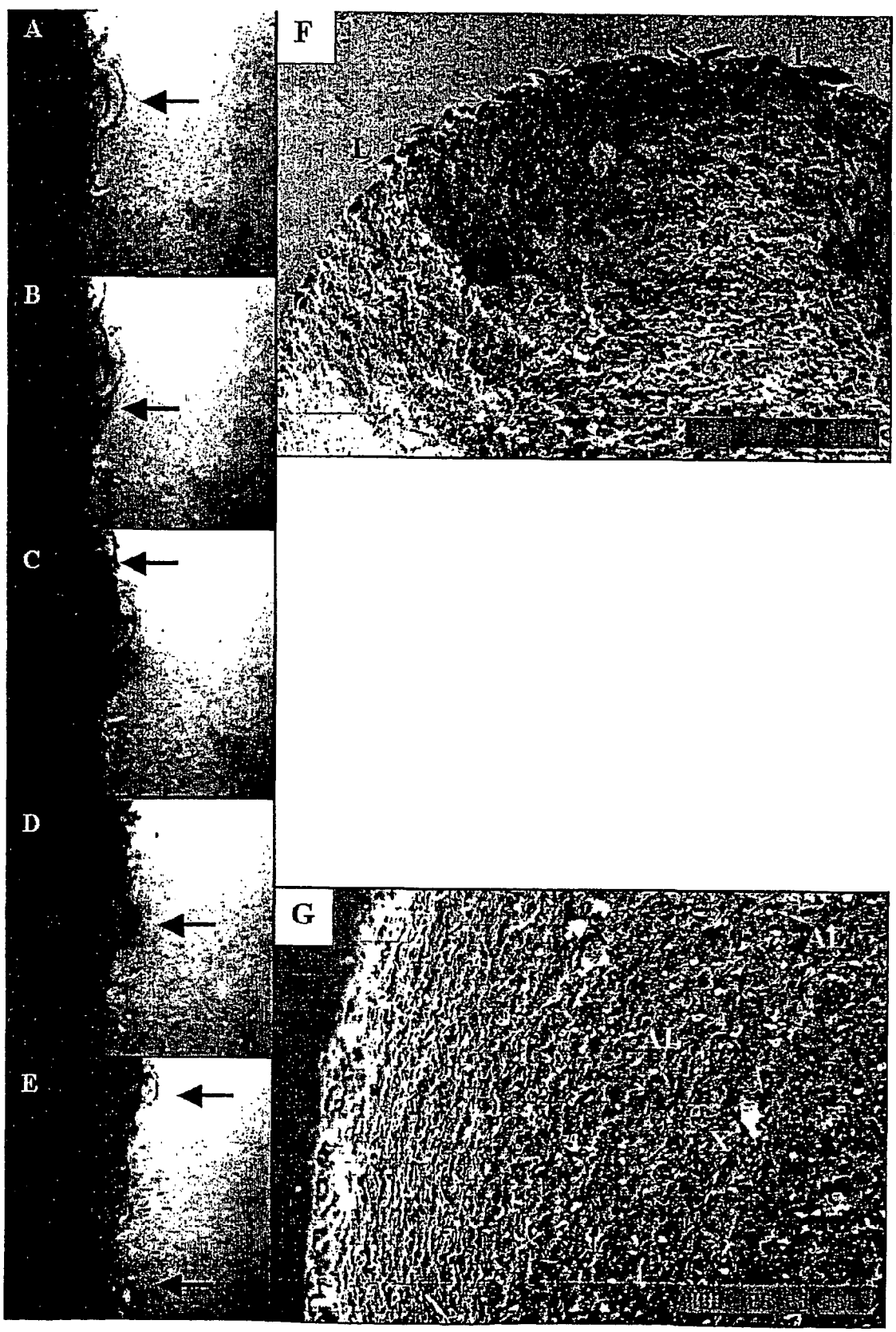
Figures 2, 7:
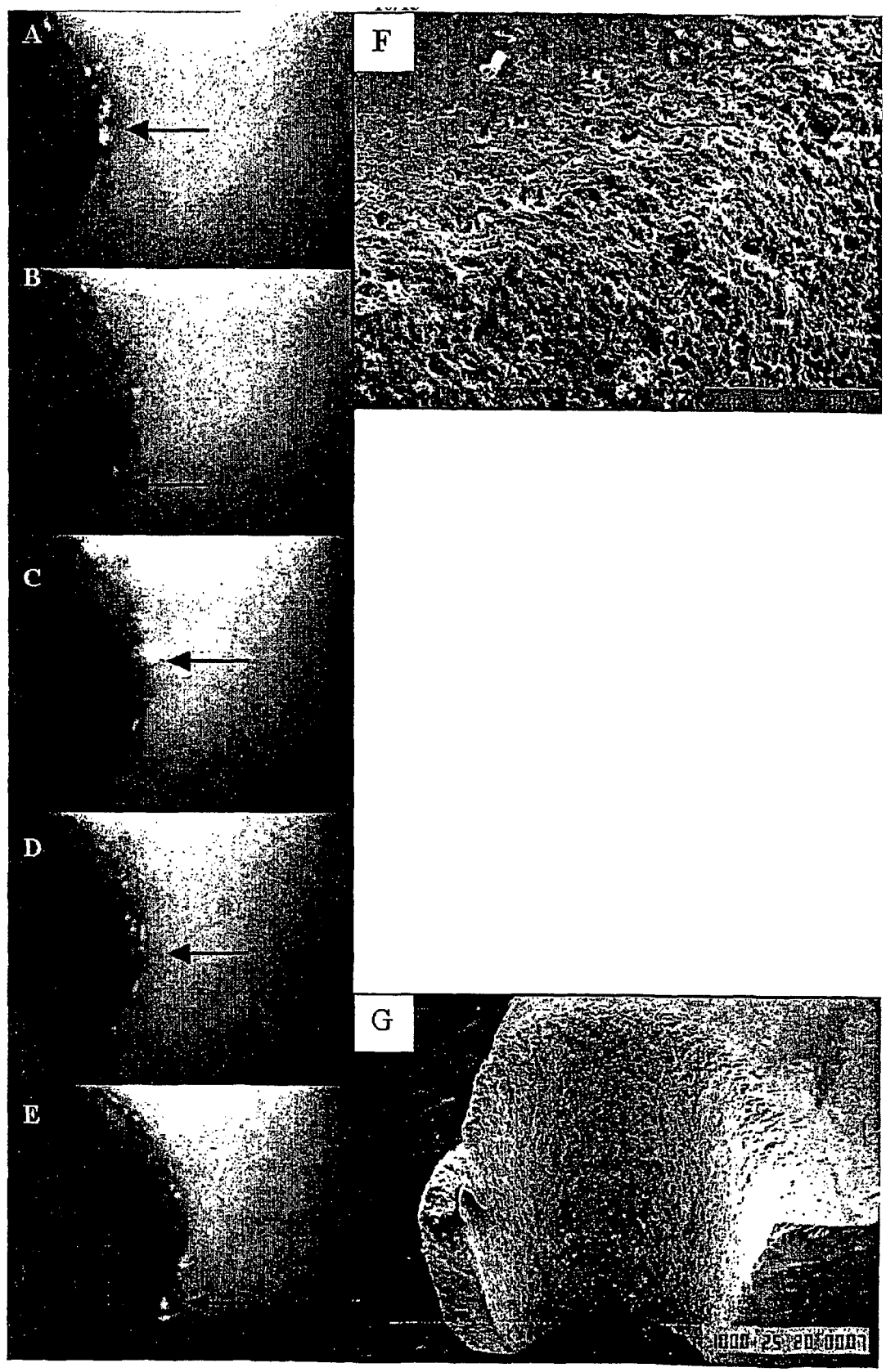

45S5 Bioglass®—(FIG. 7-1)

45S5 bioactive glass monoliths were cut extremely easily and well using this system. Recurrent re-entry patterns of fracture were seen during the real-time image analyses performed after each cutting action. Unlike the rotary cutting finished surface patterns, there was no evidence of the pattern of silicon laminae within the glass—rather, a roughened amorphous surface, with a well defined but rounded cavo-surface angle. No evidence was seen of fractures radiating into the bulk substrate.

The cut surfaces appeared clean on first inspection but traces of alumina (small, (sub)-micron proportioned particles, presumably left after abrasive particles impacted and perhaps shattered), were found using energy dispersive spectra (EDXA) on SEM examination of residual surfaces.

58S Sol-Gel Bioactive Glass—(FIG. 7-2)

58S sol-gel bioactive glass cut equally well and brittle substrate failure occurred in exactly the same manner as described above for the 45S5 Bioglass®. Similarly well-delineated but rounded cavo-surface angles at both entry and exit sides were found and delaminating flakes of swarf were again identified during pauses in the cutting activity. No catastrophic specimen fractures were identified during any cutting sequence.

The sol-gel glass monolith is a porous matrix, unlike melt derived 45S5 bioactive glass. On first inspection of the residual cut surfaces, a similarly amorphous, chipped and roughened surface was apparent. Closer surface inspection suggested the inherent pore matrix may still be patent, the concern being that cutting debris obstruction (akin to smear layers when rotary cutting dentine) would drastically reduce tissue fluid accessible glass reaction interstices, drastically altering the glass monolith's bioactive reaction kinetics.

This work confirmed the previously hypothesised highly localised brittle pattern re-entrant fracture theory (Horiguchi S., Yamada T., Inokoshi S., Tagami J., 1998, Operative Dentistry, 23, 236–243) by direct observations on brittle substrates in real time, further supported by imaging the swarf and residual surfaces seen during and just after cutting (Cook R. J., Azzopardi A., Thompson I. D., Watson T. F., 2001, The cutting Edge of Air Abrasion. Procs Far East Asia Second Symposium on Confocal Microscopy Sun-Yat Sen University, Taiwan. In Press and Cook R. J., Azzopardi A., Thompson I. D., Watson T. F., 2001, J. Microsc., 203, 199–207). The kinetic energy transferred from each alumina particle impact is minimal compared with either the overall target mass or the crude blades and embedded crystals of typical rotary cutting instruments, so minimising the likelihood of catastrophic substrate failure during machining.

Bioglass Air Abrasion Cutting (1)

Apparatus

The open jig alignment apparatus referred to above (FIG. 5), was employed in these experiments. One side of a series of five 58S sol-gel monoliths (1 cm×1 cm×3 mm) were subjected to a 5 second cutting action using an alumina abrasive, while the remaining sides were subjected to an equivalent duration of air abrasion, using similar size range (20–90 µm) 45S5 Bioglass® particles, accelerated at the same 80 psi pressure and projected through the same 600 µm diameter nozzle, at a nominal 5 nm range of nozzle to target surface, under constant delivery rate of 0.01 g/sec. The two sides of each test substrate specimen were isolated using a razor blade, protecting each surface from the effects of the alternative treatment. All air abrasion cutting activities were conducted within a purpose built, self evacuating chamber to minimise environmental pollution (Handler, Westfield, N.J., USA).

Between abrasive treatments, and after allowing 2 mins of passing clean air to clear residual cutting abrasive from the system, no particulate was detected in the cutting air stream and the abrasive was changed from alumina to the 45S5 Bioglass powder. The resulting cut specimens were blown clean with compressed air and were committed for carbon coating and SEM examination to allow characterisation and comparison of the residual finished surfaces.

To provide a complete characterisation of the air abrasive cutting process as applied to 58S sol-gel bioactive glasses and to compare impact patterns with those already known for alumina, additional 58S monoliths were exposed firstly to perpendicular 3 second bursts of Bioglass® abrasive at a constant acceleration pressure of 80 psi, but with increasing nozzle-target distances (0–8 mm), then subsequently, the acceleration pressure was decreased to 60 psi at 2 & 4 mm ranges. The treated 58S surfaces were subjected to SEM examination to demonstrate the margins and cutting depths achieved by both acceleration pressure and range.

Results

Figure 8:
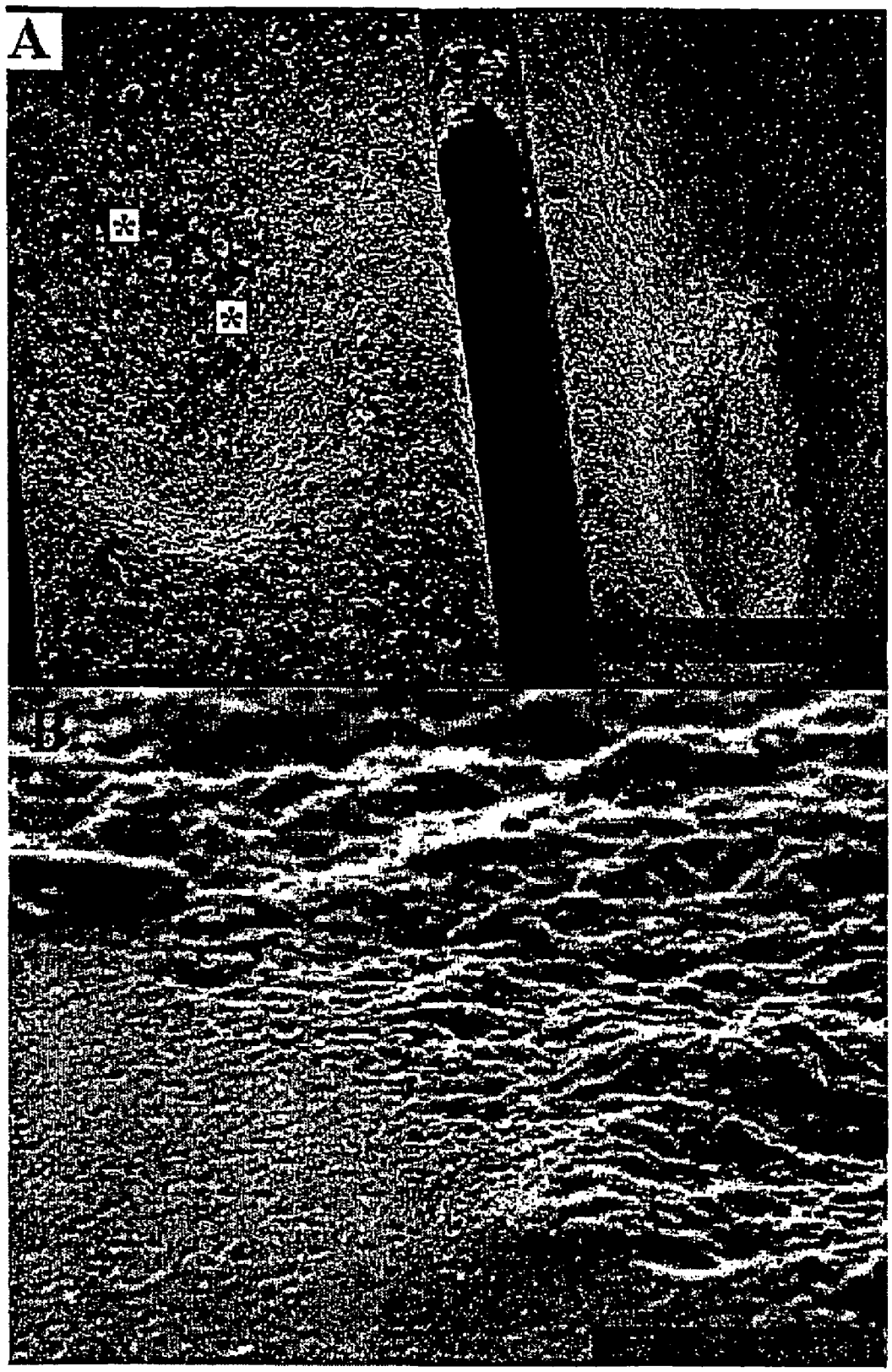
FIG. 8 illustrates two tynes of a 58S sol-gel bioactive glass comb one abraded with 45S5 bioactive glass (left) and the other with alumina (right), viewed under SEM. Deposition of bioactive cutting particle debris (*) and evidence of impacted alumina residue can be seen on the cut surfaces. Higher magnification of the cutting margin (B), shows an apparently still patent pore network. (Field widths~4 mm in A & 500 µm in B).

FIG. 8 demonstrates that while not cutting so rapidly as alumina particles, the Bioglass® abrasive did achieve a very distinct cutting action against the sol-gel substrate. 45S5 bioglass particles are embedded in/on the finished surface as were the more angular alumina cutting particles—indeed a plug of alumina was left in the cut well of the representative sample imaged. Close examination of the Bioglass® air-abrasion finish surface showed an apparently retained open pore network and the classically amorphous, chipped finished surface characteristic of air abrasion cutting (Goldstein R., Parkins F., 1994, J. Am. Dent. Assn., 125, 551–557, Laurell K A, Hess J., 1995, Quintessence, 26 (2), 139–143, Banerjee A., Kidd E., Watson T., 2000, J. Dentistry, 28, 179–186, Cook R. J., Azzopardi A., Thompson I. D., Watson T. F., 2001, The cutting Edge of Air Abrasion. Procs Far East Asia Second Symposium on Confocal Microscopy Sun-Yat Sen University, Taiwan. In Press, Cook R. J., Azzopardi A., Thompson I. D., Watson T. F., 2001, J. Microsc., 203, 199–207). When compared to the obviously poisoned surfaces from rotary cutting experiments the advantages of this cutting technique are clear.

Figure 9:
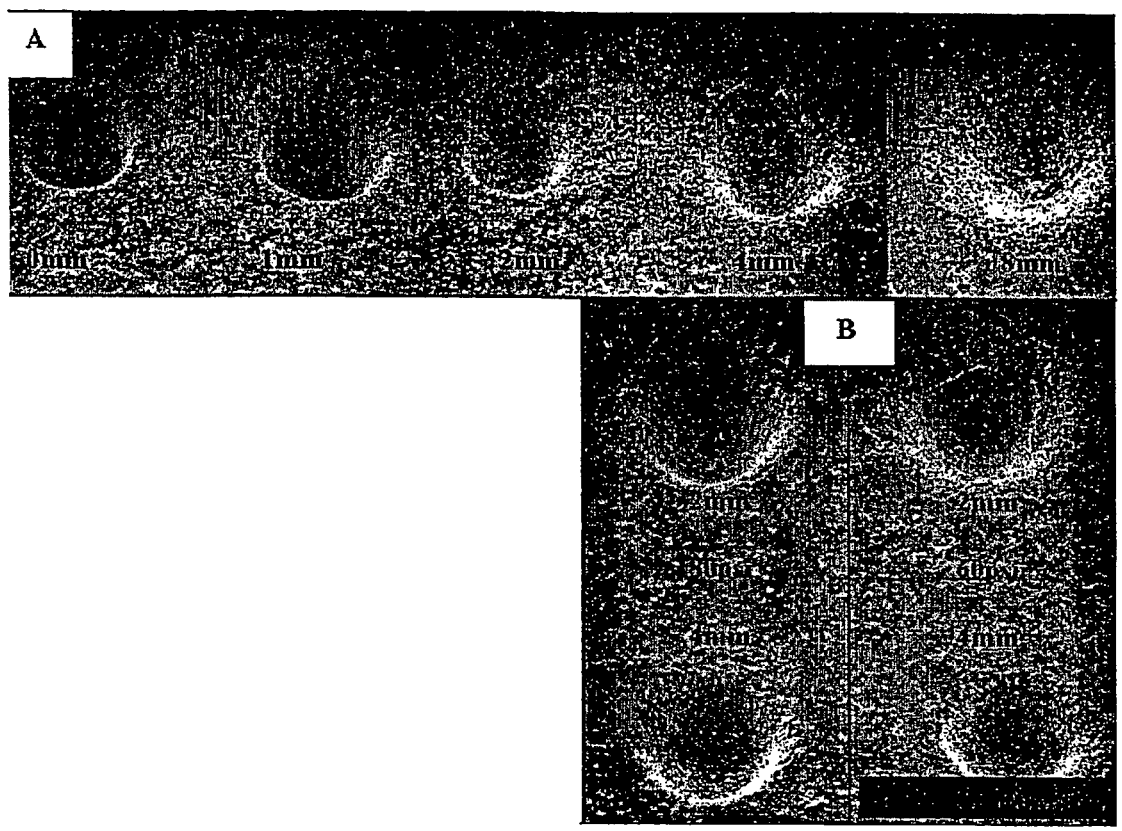
FIG. 9 illustrates the effects of cutting with bioglass abrasive. A: Composite image from one substrate block viewed at a constant distance, showing the effect of progressive separation of air abrader nozzle and target (distances shown) at a constant Bioglass® abrasive feed rate and acceleration pressure (80 psi) (Field width~1 cm). B: Composite image showing that the decrease in accelerant pressure reduces cutting depth and thus efficiency, the separation effect also being sustained, regardless of acceleration pressure (Field width~5 mm).

The results of the second phase of this experiment (FIG. 9) confirmed that with reduced pressures and increased distances of the nozzle from the target surface, the cavo-surface angle of the cut bore becomes more obtuse, less well defined and the depth of the cut decreases.

The kinetic energy transferred from each Bioglass® particle impact is minimal compared with either the overall target mass or the crude blades and embedded crystals of typical rotary cutting instruments, so minimising the likelihood of catastrophic substrate failure during machining. By way of confirmation, no catastrophic specimen fractures were identified during any cutting sequence, thus commending the air abrasion method for accurately dry cutting and shaping difficult, vulnerable, brittle, moisture and heat sensitive materials, leaving rounded stress lowering margins, ideal for brittle materials and also with regard to the bioactivity of the residual surfaces, untainted by alumina fragments and cutting debris.

Bioglass Air Abrasion Cutting (2)

Apparatus

Using the same experimental design, equipment and set up as used in the Alumina air abrasion cutting above, but substituting a similar size range particulate of 45S5 Bioglass for the more conventional 27 µm grit alumina particulate, specimens of 58S sol-gel substrate glass were subjected to air abrasive cutting and real-time confocal imaging in the conventional way described.

Figure 10:
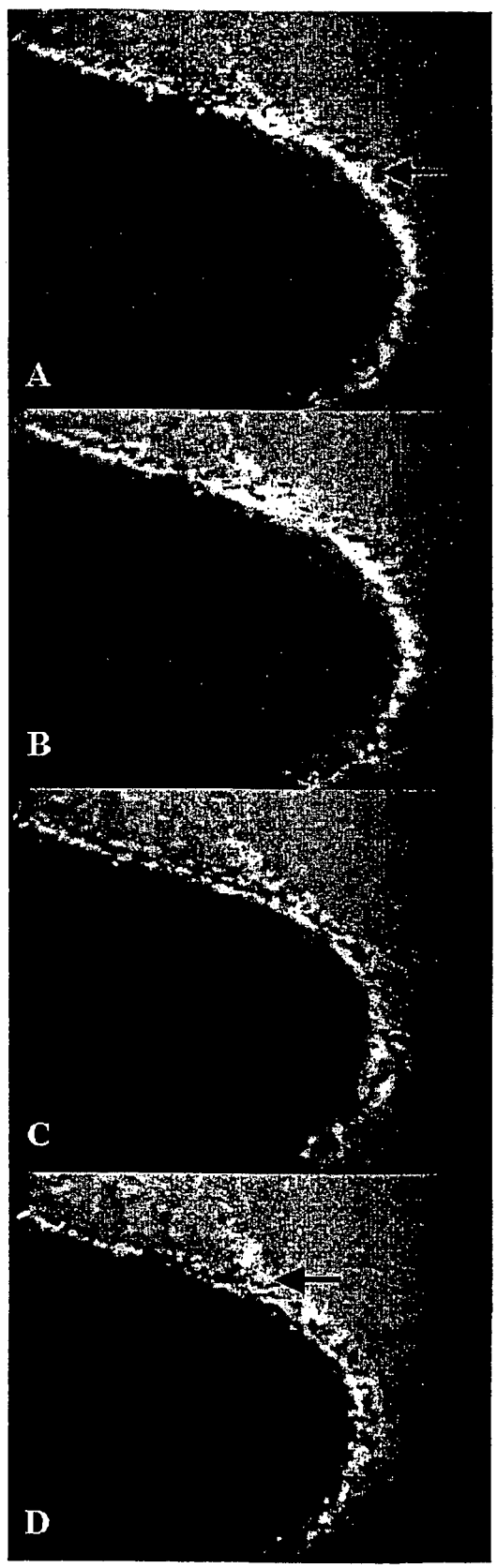
FIG. 10 illustrates air abrasive cutting (LtoR) of 58S bioactive sol-gel glass using 45S5 Bioglass® particulate as the abrasive material. A–D: ×16 serial real-time confocal images (at approximately 20 msec intervals) of the cutting front, demonstrating re-entrant fractures (arrowed) as the cutting mechanism progresses through the substrate (Field width~400 µm: ×16/0.45 na lens).

Results—(FIG. 10)

The confocal images in FIG. 10 confirm by their similarity to those in FIGS. 7-1 and 7-2 that the cutting mechanism of one bioactive glass against another is fundamentally the same as that applicable to alumina abrasive cutting into the same brittle substrate. Re-entrant fractures can be seen at the cutting edge, whose advance rate, although rapid, was not quite as efficient as if alumina had been used. The 45S5 particles used were more rounded in shape than the alumina, which along with their lower hardness, would account for this result. However, useful, accurate cutting has been demonstrated, without the risk of residual surface toxicity.

By observing the cut edges and the nature of the walls of the holes produced, just behind the active cutting face, this method has indicated that the purely end cutting process, just like that seen in the alumina cutting work undertaken by Cook et al (Cook R. J., Azzopardi A., Thompson I. D., Watson T. F., 2001, The cutting Edge of Air Abrasion. Procs Far East Asia Second Symposium on Confocal Microscopy Sun-Yat Sen University, Taiwan. In Press and Cook R. J., Azzopardi A., Thompson I. D., Watson T. F., 2001, J. Microsc., 203, 199–207), also applies to the Bioglass® cutting particulates too, as the identical surface morphologies and cutting behaviours are seen in both groups.

It would appear to be more efficient to machine a slot or reduce a surface level by making multiple passes over the target, rather than to achieve a finished depth and then to move laterally, as the cutting mechanism is a principally end-cutting phenomenon (Cook R. J., Azzopardi A., Thompson I. D., Watson T. F., 2001, The cutting Edge of Air Abrasion. Procs Far East Asia Second Symposium on Confocal Microscopy Sun-Yat Sen University, Taiwan. *In Press* and Cook R. J., Azzopardi A., Thompson I. D., Watson T. F., 2001, J. Microsc., 203, 199–207). Any opening out will allow adequate exhausting to be established and maintained. Successive passes may be made equally efficient by advancing the airbrader nozzle toward the target, maintaining an optimal separation. More rounded finish contours can simply be achieved by increasing the separation of nozzle and target. Flattened slit like air abrasive nozzles have been manufactured in the past and were reportedly capable of cutting extremely fine slots, or even sectioning materials for microscopy (Boyde A., J. Dent. Res., 1963, vol. 42, p 1115). However, the round orifice is most likely to be chosen for general-purpose work, as this allows any shape of cavity to be machined with least operator concern over varying orientations of the nozzle axes and the target.

Figure 12:
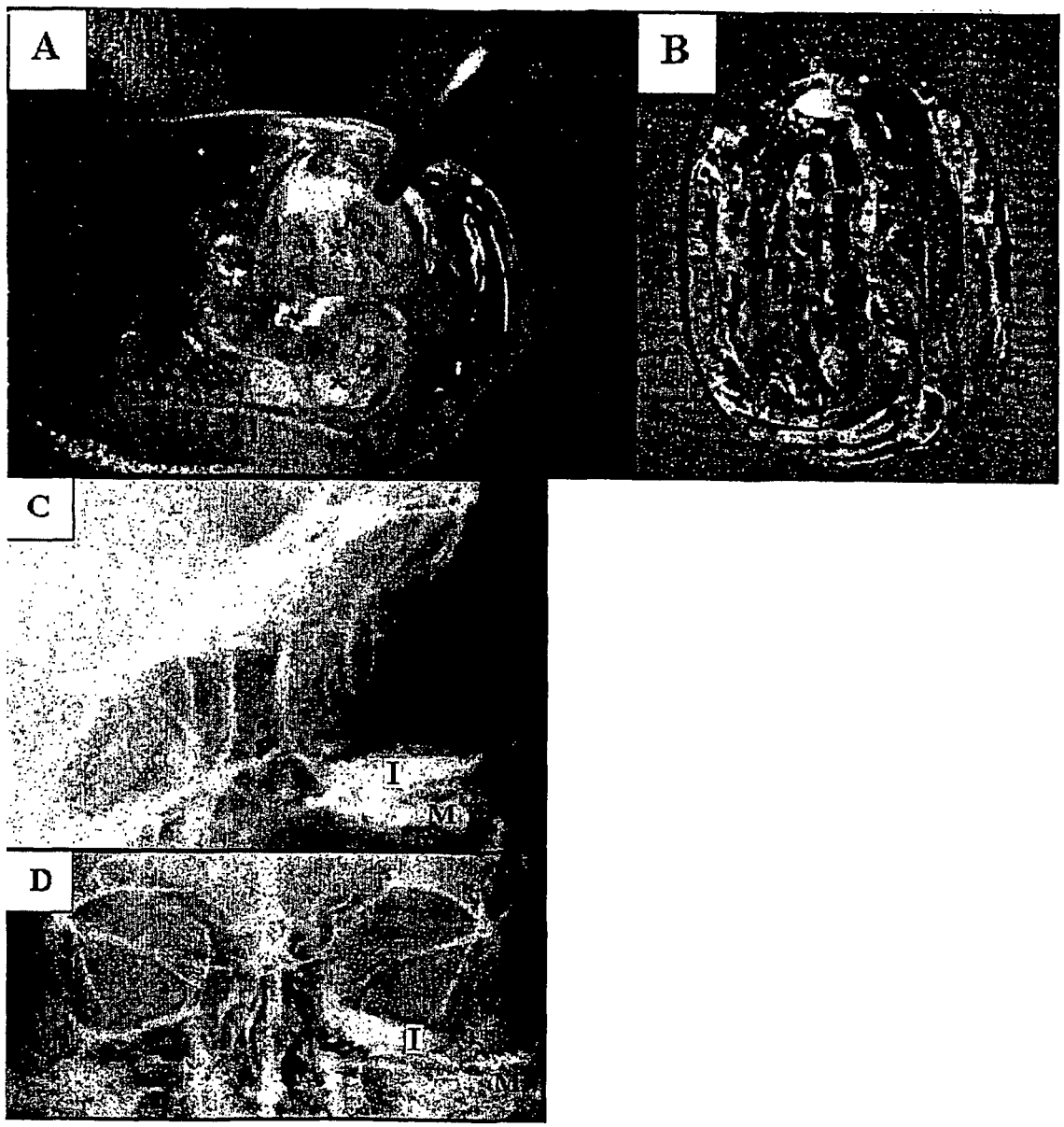
FIG. 12. illustrates a bioactive glass monolith trimmed and with suture holes (*) bored using bioactive glass air abrasive techniques (A) leaving an intact implant after sterilisation (B). One week post-operative Radiographic views show the Lateral Cephalograph (C) and PA skull (D) views. The glass implant (I) sits, tucked behind the bony infra orbital rim. There is no evidence of fracture or damage to the bespoke shaped implant mass. The titanium miniplate (M) is a "left over" from the initial surgery 2 years prior to the bioactive implant surgery.

Clinical Application (FIG. 12)

After the failure of conventional therapy methods for post traumatic orbital volume increase, a decision was taken to reconstruct the floor of a patient's eye socket with a 45S5 bioactive glass monolith implant. Pre-operatively, a series of 5 custom made bioactive glass monoliths were conventionally cast using a bespoke graphite mould and plug technique. The mould shape was established by hand copying profiles from a dried human skull for the superior contours, the known volume deficit within the patient's damaged orbit and inferior contours being interpreted from the CT information. Glass monoliths of approximately 2×3.5 cm and varying from 4–8 mm depth (mean volume=4.2 ml), were thus produced (See FIG. 12).

After casting, further monolith shaping was successfully conducted, using the air abrasion cutting technology described above. Suture holes were then bored (See FIG. 12) also using the bioactive glass air abrasion technique. The monoliths were then subjected to routine pre-operative hospital standard sterilising processes.

Surgical access to the patient's orbital floor was achieved via a pre-existing infra-orbital incision, and the sub-periosteal implant was firmly sutured into place using un-dyed 3/0 Vicryl® suture, passing through both the implant holes provided and a pair of small bur holes in the inferior bony orbital rim of the patient.

Radiographic examination confirmed accurate placement and stability of the Bioglass® implant, while also revealing how good the implant—bone fit was (See FIG. 12). Follow up, at six months after placement, confirmed the total success of the procedure and the stability and sustained integrity of the shape of the implant.

The invention claimed is:

1. A method of cutting a bioactive glass object which comprises contacting the bioactive glass object with bioactive glass particles delivered using an air abrasion system.

2. A method of cutting a bioactive glass object which comprises contacting the bioactive glass object with bioactive glass particles delivered using an air abrasion system, wherein the bioactive glass object forms part of a medical or surgical implant.

3. A method of cutting a bioactive glass object which comprises contacting the bioactive glass object with bioactive glass particles delivered using an air abrasion system, wherein the bioactive glass object is formed from more than one bioactive glass.

4. A method of cutting a bioactive glass object which comprises contacting the bioactive glass object with bioactive glass particles delivered using an air abrasion system, wherein the bioactive glass particles comprises a source of $SiO_2$ or $Si(OH)_2$, and a source of CaO or $P_2O_5$.

5. A method of cutting a bioactive glass object which comprises contacting the bioactive glass object with bioactive glass particles delivered using an air abrasion system, wherein the bioactive glass particles further comprises at least one hardening agent and/or at least one softening agent.

6. A method according to claim 5 wherein the softening agent is selected from Na, K, Ca, Mg, B, Al, P, N, F and the hardening agent is $TiO_2$.

7. A method of cutting a bioactive glass object which comprises contacting the bioactive glass object with bioactive glass particles delivered using an air abrasion system, wherein the bioactive glass particles comprises 1 to 100% $SiO_2$ or $Si(OH)_2$, 0–60% CaO, 0 to 60% $P_2O_5$, 0 to 45% $Na_2O$, 0 to 45% $K_2O$ and 0 to 40% MgO.

8. A method of cutting a bioactive glass object which comprises contacting the bioactive glass object with bioactive glass particles delivered using an air abrasion system, wherein the bioactive glass particles are obtainable by Sol-Gel method.

9. A method according to claim 8, wherein the bioactive glass particles comprises 44 to 86 weight % $SiO_2$, 4 to 46 weight % CaO and 3 to 15 weight % $P_2O_5$.

10. A method to claim 8, wherein the bioactive glass particles comprises 58 weight % $SiO_2$, 33 weight % CaO and 9 weight % $P_2O_5$.

11. A method of cutting a bioactive glass object which comprises contacting the bioactive glass object with bioactive glass particles delivered using an air abrasion system, wherein the bioactive glass particles are obtainable by the Melt method.

12. A method according to claim 11, wherein the bioactive glass particles comprises 47 to 51 weight % $SiO_2$ 23 to 25 weight % CaO, 23 to 25 weight % $Na_2O$ and 0 to 6 weight % $P_2O_5$.

13. A method according to claim 11, wherein the bioactive glass particles comprises (by weight):
$SiO_2$—45%
$Na_2O$—24.5%
CaO—24.5%
$P_2O_5$—6%.

14. A method of cutting a bioactive glass object which comprises contacting the bioactive glass object with bioactive glass particles delivered using an air abrasion system, wherein the bioactive glass particles have a Vickers Hardness of at least that of the bioactive glass object.

15. A method of cutting a bioactive glass object which comprises contacting the bioactive glass object with bioactive glass particles delivered using an air abrasion system, wherein the bioactive glass particles are substantially non-spherical.

16. A method of cutting a bioactive glass object which comprises contacting the bioactive glass object with bioactive glass particles delivered using an air abrasion system, wherein the bioactive glass particles are substantially spherical.

17. A method of cutting a bioactive glass object which comprises contacting the bioactive glass object with bioactive glass particles delivered using an air abrasion system, wherein the bioactive glass particles have a diameter of from 10 μm to 500 μm.

18. A bioactive glass surgical or dental implant cut according to a method of cutting a bioactive glass object which comprises contacting the bioactive glass object with bioactive glass particles delivered using an air abrasion system.

* * * * *